United States Patent [19]

Kagenow et al.

[11] Patent Number: 5,208,147
[45] Date of Patent: May 4, 1993

[54] MEANS FOR MEASURING A CHARACTERISTIC IN A SAMPLE FLUID

[75] Inventors: Henrik Kagenow, Farum; Anne R. Eisenhardt, Horsholm, both of Denmark

[73] Assignee: Radiometer A/S, Copenhagen, Denmark

[21] Appl. No.: 884,703

[22] Filed: May 18, 1992

Related U.S. Application Data

[63] Continuation of Ser. No. 689,727, Apr. 22, 1991, Pat. No. 5,114,859, which is a continuation of Ser. No. 608,012, Oct. 31, 1990, abandoned, which is a continuation of Ser. No. 238,556, Aug. 30, 1988, abandoned.

[30] Foreign Application Priority Data

Jul. 21, 1988 [DK] Denmark ............... 4091/88

[51] Int. Cl.$^5$ ............... C12Q 1/54; G01N 21/00
[52] U.S. Cl. ............... 435/14; 422/58; 422/101; 436/85; 436/177
[58] Field of Search ............... 422/58, 181; 435/14; 436/95, 177

[56] References Cited

U.S. PATENT DOCUMENTS

| | | | |
|---|---|---|---|
| 4,477,575 | 10/1984 | Vogel et al. | 436/170 |
| 4,753,776 | 6/1988 | Hillman et al. | 422/101 |
| 4,786,603 | 11/1988 | Wielinger et al. | 436/69 |
| 4,816,224 | 3/1989 | Vogel et al. | 436/177 X |
| 4,892,834 | 1/1990 | Rouh | 422/58 X |

FOREIGN PATENT DOCUMENTS 0133895  3/1985 .

OTHER PUBLICATIONS

Abstract: EP269240 (Jun. 1, 1988)–Corresponds to US 4,753,776 (Hillman et al).
Abstract: EP208218 (Jan. 14, 1987)–Corresponds to US 4,786,603 (Wielinger et al).
Abstract: WO8702267 (Apr. 23, 1987).
Abstract: EP207360 (Jan. 7, 1987).
Abstract: DE3508427 (Sep. 11, 1986).
Abstract: DE3441149 (May 15, 1986).
Abstract: JP60066164 (Apr. 16, 1985).
Abstract: EP130335 (Jan. 9, 1985).
Abstract: DE3323973 (Jan. 3, 1985).
Abstract: DE3247608 (Jul. 5, 1984).
Abstract: DE3130749 (Feb. 24, 1983).
Abstract: US4816224 (Mar. 28, 1989).
Abstract: BE878245 (Feb. 14, 1980).
Abstract: DE1598048 (Jun. 16, 1977).
Abstract: DE2118455 (Apr. 16, 1971).
Abstract: US3552928.

*Primary Examiner*—Charles Hart
*Attorney, Agent, or Firm*—Bryan Cave

[57] ABSTRACT

A measuring device, intended for measurements on whole blood, comprises a sample fluid chamber for containing a blood sample, ion-selective potentiometric electrodes for measurement of the concentrations of sodium and potassium ions, a reference potentiometric electrode, an optical sensor for measuring the concentration of glucose by means of a color reaction, a cuvette having a window permitting spectrophotometric measurement of the level of haemoglobin, a conditioning (calibration) fluid chamber in which the ion-selective electrodes and the reference electrode are exposed to a conditioning (calibration) fluid comprising known concentrations of sodium and potassium ions (thereby facilitating calibration of the response of the ion-selective electrodes), a rupturable pack containing the conditioning fluid and from which the fluid is released into the conditioning fluid chamber upon application of pressure to the pack, and a wall part which partly defines the sample fluid chamber and has weakened areas which are ruptured upon movement of the sensors (i.e. the electrodes and the glucose sensor) so as bring the sensors into contact with the blood sample and which establishes a seal around the sensors.

4 Claims, 3 Drawing Sheets

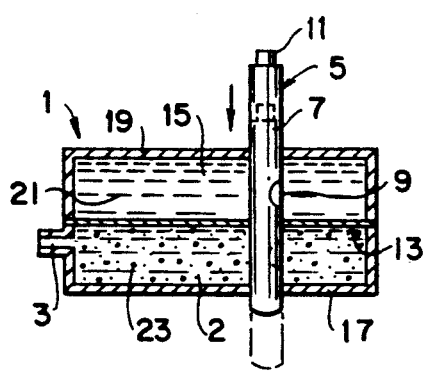
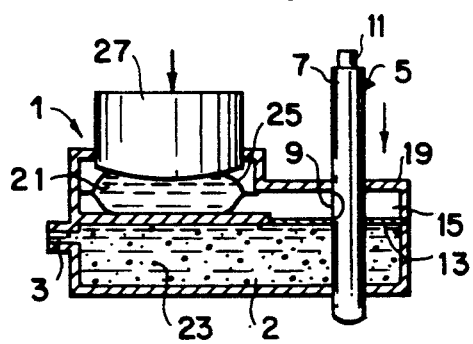
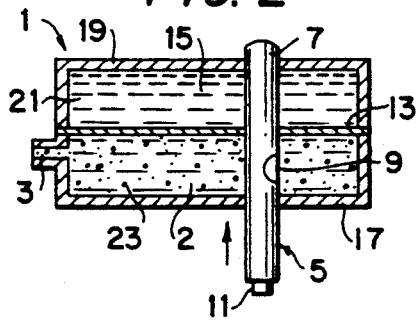
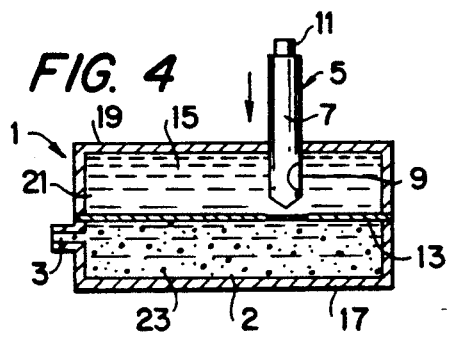
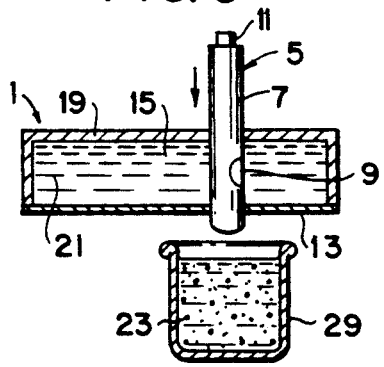
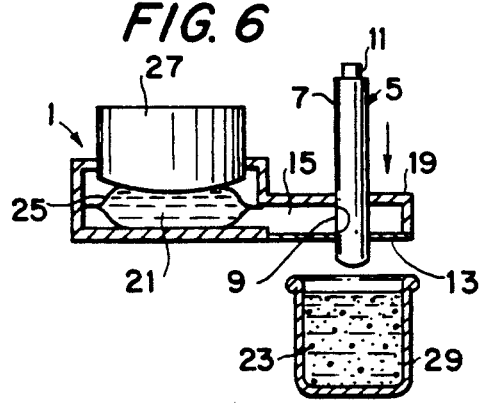
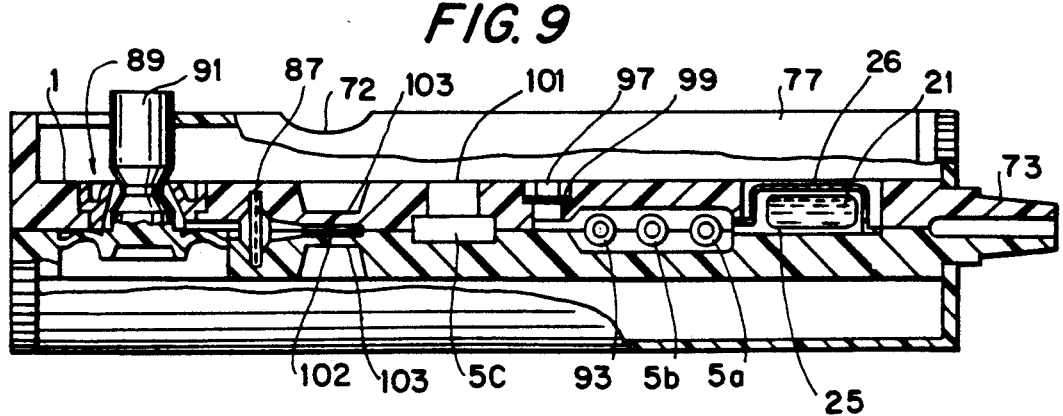

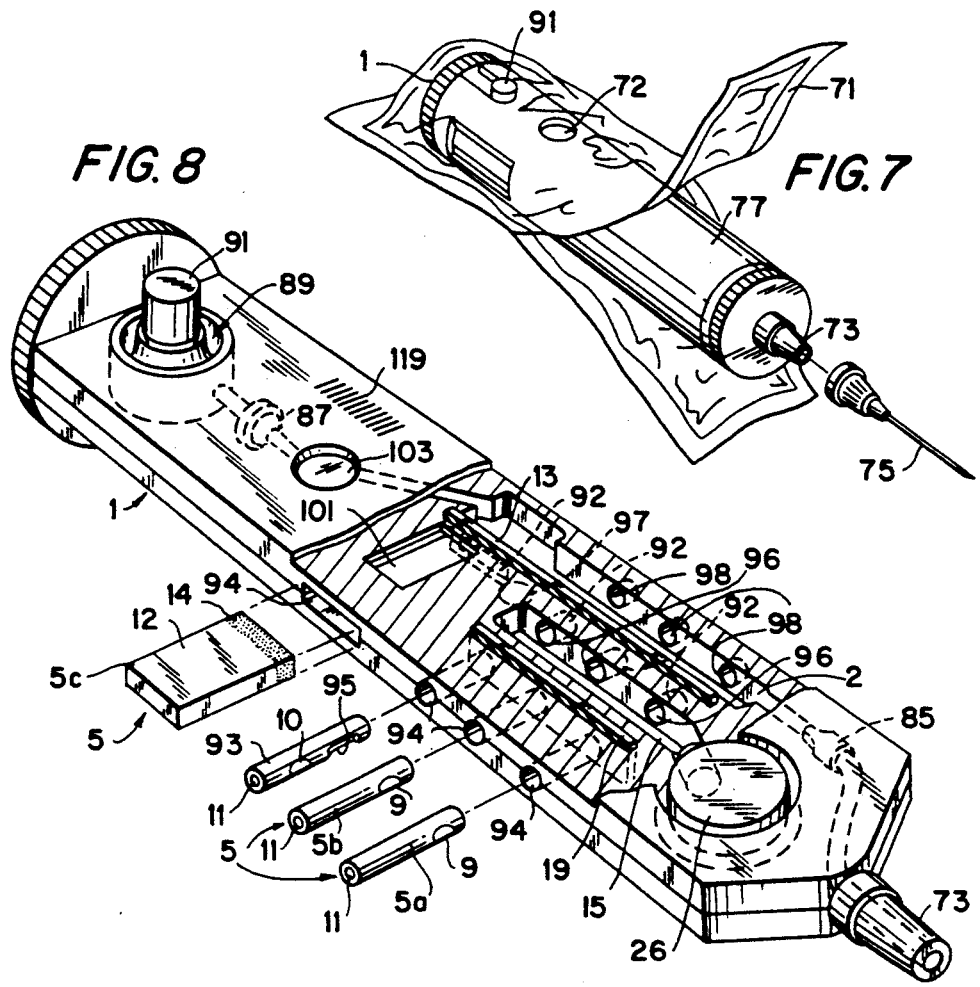
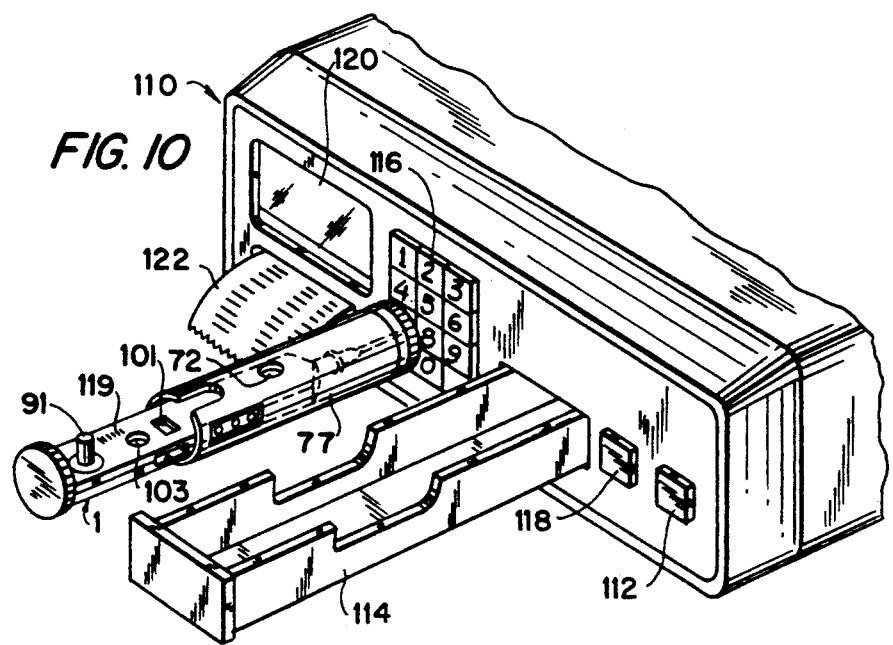

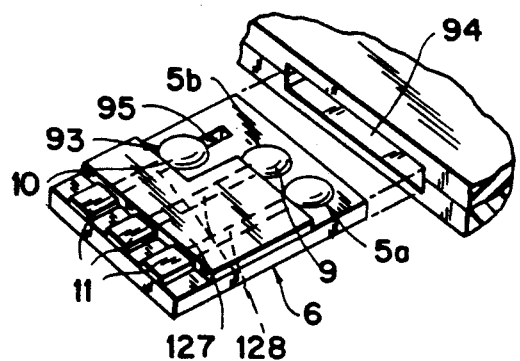
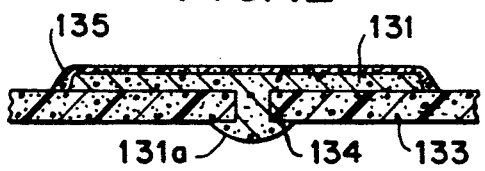
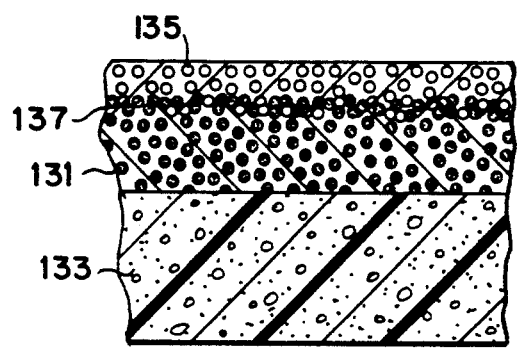
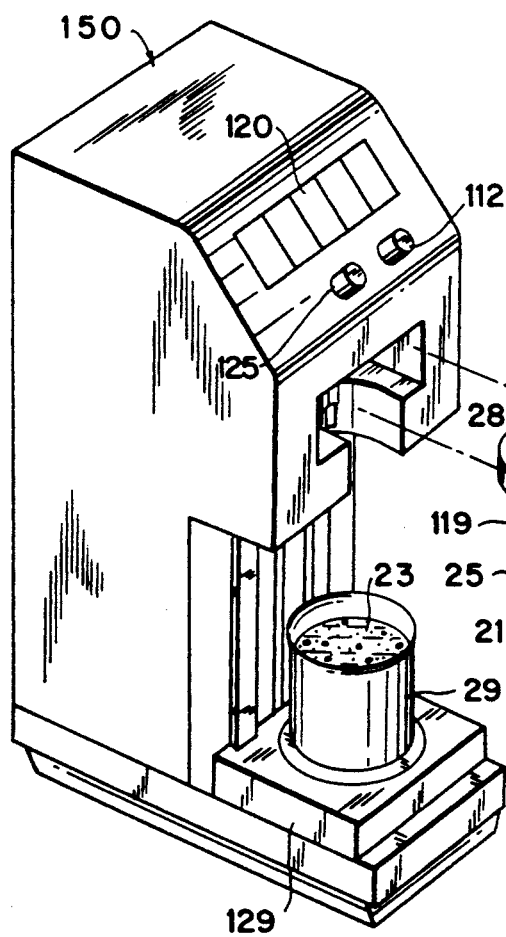
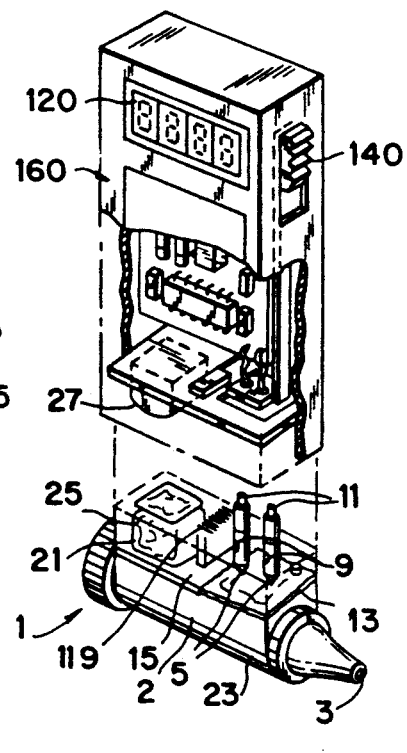

MEANS FOR MEASURING A CHARACTERISTIC IN A SAMPLE FLUID

This is a continuation of U.S. application Ser. No. 07/689,727 filed Apr. 22, 1991, U.S. Pat. No. 5,114,854, which is a continuation of U.S. application Ser. No. 07/608,012 filed Oct. 31, 1990, now abandoned which is a continuation of U.S. application Ser. No. 07/238,556 filed Aug. 30, 1988 now abandoned.

FIELD OF THE INVENTION

The present invention relates to a method for measuring a characteristic which is a function of the concentration of one or more chemical species in a sample fluid, examples of such characteristics being concentration itself, electrical conductivity and ionic strength, to measuring devices which may be used in the methods, to analysis systems comprising such a measuring device, and to an analyzer adapted to accommodate the measuring device. The invention has applicability particularly in the field of clinical analysis, but also, for example, in wet chemical analysis in general, and in gas analysis.

BACKGROUND OF THE INVENTION

In human medicine, it has hitherto been customary practice to send samples of body fluids, e.g. blood, plasma or urine, for analysis to a specialized clinical laboratory possessing the necessary technical equipment and trained staff. Clinical chemical parameters of particular interest are, for example:

pH.

concentrations of electrolytes, such as $Li^+$, $Na^+$, $K^+$, $Ca^{2+}$, $Mg^{2+}$, $Cl^-$, $HCO_3^-$ and $NH_3$ ($NH_4^+$), concentrations of dissolved gases, notably oxygen and carbon dioxide (conventionally reported in the form of partial pressures, e.g. $pO_2$, $pCO_2$), haemoglobin concentration, concentrations of metabolic factors, such as glucose, creatinine, urea (BUN), uric acid, lactic acid, pyruvic acid, ascorbic acid, phosphate, protein, bilirubin, cholesterol, triglycerides, phenylalanine and tyrosine, concentrations of enzymes, such as lactic acid dehydrogenase (LDH), lipase, amylase, choline esterase, alkaline phosphatase, acid phosphatase, alanine amino transferase (ALAT), aspartate amino transferase (ASAT) and creatinine kinase (CK).

and concentrations of ligands, such as antibodies and nucleotide fragments.

In the past, clinical chemical analysis systems have tended to be large in size, expensive and complex to operate, and in general only relatively large medical institutions have been able to afford the purchase, operation and maintenance of such systems. Smaller hospitals, clinics, general practitioners etc. usually have had to employ centralized commercial or hospital laboratories for clinical chemical analyses, leading to unavoidable delays in the procedure.

Since abnormal values of certain clinical chemical parameters are indicative of serious danger to health, the rapid and reliable determination of clinical chemical parameters in general is of crucial importance for proper and effective medical treatment. Furthermore, quite apart from the acute aspects of medical treatment, it is clearly an advantage, both for patients from a psychological viewpoint and for medical staff from an administrative viewpoint, that clinical analysis results are accessible as quickly as possible.

Thus, increasing demands for reduction in costs, more rapid turnover, greater decentralisation and increased staff flexibility in clinical chemical analysis have provided an incentive for the development of easy-to-use, easy-to-maintain, reliable, relatively cheap, compact and, if possible, portable equipment, based in part on discardable components, for the bedside measurement of those characteristics of chemical species which constitute fundamental clinical chemical parameters of body fluids.

Equipment based in part on disposable components may also be of great value in numerous non-medical analytical applications where the ability to carry out decentralised or field analyses is of importance. Examples of such applications are the determination of pH, colour and concentrations of chemical species such as chloride, nitrite, nitrate, sulfate and phosphate in relation to control of the quality of bodies of water used for domestic supplies, and on-site analyses of the contents of process vessels, e.g. in fermentation processes such as the production of beers and wines, in sugar refining and in industrial syntheses.

PCT applications WO 85/02257, WO 85/04719 and WO 86/05590, U.S. Pat. No. 4,436,610, U.S. Pat. No. 4,225,410 and European application EP 0189316, disclose apparatuses, all of which comprise a disposable measuring device and an analyzer, suitable for bedside clinical chemical analyses, notably of blood samples. European patent EP 0012031 discloses a method and apparatus for measuring a chemical characteristic of a liquid, in particular for measuring the pH of a blood sample. The preferred embodiments of the measuring devices disclosed in the first five of the above mentioned sources are intended for discardment after a single use, whereas a preferred embodiment disclosed in EP 0189316 and embodiments disclosed in EP 0012031 are intended to be disposed of after repeated use. In each of these devices the sensor or sensors responsive to the chemical species, and the chamber(s) or passage(s) in which the sensor or sensors are exposed to a calibration fluid or a sample fluid remain fixed with respect to the housing or support of the measuring device as a whole.

British application GB 2 183 041 discloses apparatus comprising an analyzer and a measuring device for analyzing an undiluted body fluid; the measuring device comprises an ion-selective or enzymatic sensing electrode which is mounted on a probe, the probe being movable to transfer the sensing electrode between an open-ended reference wash cell and a sample cup bearing the body fluid specimen to be analyzed. The measuring device disclosed is intended for prolonged repeated use and is rather complex in its construction.

As will be described in detail in the following, the present invention concerns, inter alia, methods using discardable measuring devices for measuring a characteristic which is a function of the concentration of one or more chemical species in a sample fluid, for example a body fluid, the measurement entailing movement of a sensor relative to a sample fluid chamber containing a sample fluid and/or relative to a chamber containing a fluid for conditioning the sensor (e.g. calibrating the sensor response), or movement of said sample fluid chamber and/or said conditioning fluid chamber relative to a sensor. As will become clear from the following, this principle offers a number of advantages in connection with measurements using discardable measuring devices.

SUMMARY OF THE INVENTION

The present invention comprises a method for measuring a characteristic which is a function of the concentration of one or more chemical species in a sample fluid, by using a measuring device comprising a sensor having a sensing surface part, and a chamber adapted to contain a conditioning fluid, the chamber being partly defined by a first wall part adapted to allow the sensor to pass through it and establish a seal around the sensor when the sensor traverses the first wall part, the sensor and the chamber being movable relative to each other so as to transfer the sensing surface part of the sensor through the first wall part from a position where the sensing surface part of the sensor is inside the chamber to a position where it is outside the chamber, the method comprising exposing the sensing surface part of the sensor to a conditioning fluid in the chamber, moving the sensor and the chamber relative to each other so as to transfer the sensing surface part of the sensor through the first wall part and position it outside the chamber, exposing the sensing surface part of the sensor to a sample fluid, deriving the characteristic on the basis of a response generated by the sensor when the sensing surface part of the sensor is exposed to the sample fluid, and, optionally, a response generated by the sensor when the sensing surface part of the sensor is exposed to the conditioning fluid, and discarding the measuring device after one measurement of the characteristic.

Movement of the sensor and the chamber relative to each other can be achieved either by keeping the chamber fixed relative to the measuring device as a whole, and moving the sensor, or by keeping the sensor fixed relative to the measuring device as a whole, and moving the chamber.

For certain types of sensor for which the conditioning fluid serves simply as a calibration fluid for calibrating the response of the sensor in relation to the magnitude of the characteristic to be measured, the order in which the exposure of the sensing surface part of the sensor to the conditioning fluid and to the sample fluid, respectively, takes place is of no consequence for the derivation of the characteristic, for which reason the present invention further comprises a method related to that described above, wherein the sensor and the chamber are movable relative to each other so as to transfer the sensing surface part of the sensor through the first wall part from a position where the sensing surface part of the sensor is outside the chamber to a position where it is inside the chamber, the method comprising exposing the sensing surface part of the sensor to a sample fluid, moving the sensor and the chamber relative to each other so as to transfer the sensing surface part of the sensor through the first wall part and position it inside the chamber, exposing the sensing surface part of the sensor to a conditioning fluid in the chamber deriving the characteristic on the basis of a response generated by the sensor when the sensing surface part of the sensor is exposed to the sample fluid, and a response generated by the sensor when the sensing surface part of the sensor is exposed to the conditioning fluid, and discarding the measuring device after one measurement of the characteristic.

The central feature of methods according to the present invention is the use of a discardable measuring device incorporating any reagents necessary for the conditioning of the sensor, and in which the positioning of the sensor is altered from a position in which its sensing surface part is exposed to the conditioning fluid to a position where it is exposed to a sample fluid, or vice versa. Measuring devices of this type can be manufactured cheaply as small and compact units which are easy to manipulate, and which at the same time permit a high quality of measurement of the characteristic in that the sensor is subjected to a well-defined conditioning immediately before or immediately after measurement on the sample fluid, the conditioning ensuring that the characteristic is accurately derivable from the response of the sensor.

The term "fluid" as used here denotes either a liquid phase or a gaseous phase. Liquid phases, notably aqueous solutions, are the more important in connection with clinical chemical applications of the present invention, for which reason preferred embodiments of measuring devices for use according to the present invention are adapted for the measurement of characteristics of chemical species in aqueous media. These embodiments will be described and exemplified in detail in the following, although it will be evident to a person skilled in the art that the principles of the invention as disclosed herein may equally well be adapted for use in measurements on non-aqueous fluids and fluids which are gases.

The term "sensor" as used here denotes any kind of organ of which some part, in the present context called the sensing part, is capable either of selective interaction with the chemical species of interest, thereby producing a well-defined and measurable response which is a function of the desired characteristic of that chemical species, the desired characteristic thus being derivable therefrom, or of response to a bulk property of a fluid, the response not being selective with respect to any specific chemical species, but being a function of the total concentration of one or more chemical species in the fluid, the desired characteristic thus being derivable therefrom.

Relevant types of sensor are those adapted to determine any of the previously mentioned clinical chemical parameters, for example:

potentiometric sensors for use in aqueous media, such as ion-selective electrodes for specific measurement of the concentration of selected ionic chemical species [a description of non-limiting examples of some ion-selective electrodes for the selective measurement of the concentrations of a number of cations and anions of frequent interest is provided by Simon (W. Simon, "Ion-Selective Electrodes Based on Neutral Carriers", in H. Freiser, Ed., "Ion-Selective Electrodes in Analytical Chemistry", Plenum, 1978, pp. 211-281)], the response being in the form of an electric potential, amperometric sensors, such as sensors for the determination of oxygen partial pressure, whose response is in the form of an electric current, optical sensors, such as sensors producing a colour response to a particular chemical species, the colour intensity being measured by, e.g., reflectometry, piezoelectric sensors, thermometric sensors,
pressure-change sensors,
acoustic sensors,
enzyme-based sensors employing an enzymatic reaction and generating a response on the basis of any relevant physical principle, for example any of those principles employed in the sensor types listed above; examples are enzyme-based thermistors and enzyme-based amperometric sensors for use in the measurement of concentrations of metabolic products, e.g. glucose, urea, creatinine or lactate,
and affinity sensors comprising one moiety of an affinity pair, e.g. an antigen/antibody pair or two complementary nucleotide fragments, the other moiety being the chemical species of interest Sensors generally perform a conversion function to convert the energy form associated with the change occurring at the sensing surface part to electrical energy or electromagnetic radiant energy, the sensor response thereby being registerable in the form of an electrical or optical signal. A more detailed description of non-limiting examples of conversion principles which are relevant in connection with sensors is given by Middelhoek & Noorlag (S. Middelhoek & D. J. W Noorlag, "Three-Dimensional Representation of Input and Output Transducers", *Sensors and Actuators* 2, 1981/1982, pp. 29-41).

In potentiometric sensing systems, a reference electrode provides a substantially fixed value of electric potential relative to which the electric potential generated by the sensor when the sensing surface part of the sensor is exposed to a sample or conditioning fluid is measured, the desired characteristic being derived therefrom; this substantially fixed electric potential is achieved by exposure of the sensing surface part of the reference electrode to a suitable fluid, hereafter denoted a "reference fluid", of substantially fixed composition.

The necessary electrochemical connection between the reference fluid and the conditioning or sample fluid is normally established through the provision of a suitable fluid junction, permitting inter-fluid contact but substantially without mixing of the two fluids; in cases where the electrochemical connection is to be made between two liquids, this junction is often denoted a "liquid junction". The use, according to the present invention, of a potentiometric sensor thereby comprises the provision of a suitable reference electrode, reference fluid and fluid junction; as will be made clearer in the following, all of the latter can conveniently be incorporated in the measuring device.

In amperometric sensing systems, a reference electrode provides a substantially fixed value of electric potential, achieved, for example, in the same way as in potentiometric systems or by exposure directly to the sample fluid, and at the same time another electrode, the so-called "counter electrode", functions as a cathode or anode relative to a so-called "working electrode"; the electric current which passes between the working electrode and the counter electrode, both of which are directly or indirectly (e.g. via a membrane) exposed to a sample fluid, when an external electric potential is applied across the two electrodes is then measured and the desired characteristic derived therefrom. Amperometric sensors are often constructed such that the counter and reference electrodes are contained together as one electrode, hereinafter simply referred to as a "reference electrode" in connection with amperometric sensing systems.

The derivation of a characteristic, for example the concentration of a chemical species, from the response of a sensor requires that the relationship between the magnitude of the response of the sensor in question and the magnitude of the characteristic, under the conditions pertaining during the measurements, is known. Certain types of sensors can be manufactured with such a high degree of reproducibility that the relationship between response and characteristic (as generally determined by sensor sensitivity and sensor response at at least one value of the characteristic) for all the members of a production batch of the same type of sensor is substantially identical and thus predeterminable. Certain other types of sensors may be manufactured with such a degree of reproducibility that at least one of, but not all the parameters determining the relationship between response and characteristic will be predeterminable. Other aspects of sensor response, for example drift and variation with temperature, may also be predetermined. It is therefore possible for the manufacturer to equip a measuring device, incorporating such a sensor, with appropriate sensor data, together with any other desirable information, e.g. date of manufacture, expiry date, measurement cycle control information, etc., in the form of a code, such as a bar-code which can be read by an optical reading device, or a magnetic code which can be read by a magnetic reading device. Reading means for decoding the information contained in the code can advantageously be incorporated in an analyzer (as used in connection with the present invention, the term "analyzer" designates an apparatus adapted to removably accommodate the measuring device and provided with means for bringing about movement of the sensor and the sample fluid chamber relative to each other when the measuring device is accommodated in the analyzer, sensor response transmission means, and means for registering the response generated by the sensor, said sensor response transmission means facilitating communication between the sensor response output means of the and the sensor response registering means of the analyzer). Various embodiments of such an analyzer for use in an analysis system according to the present invention are described in greater detail later.

It is thus possible, using such an analyzer, to calibrate the response of the sensor in relation to the magnitude of the characteristic simply by carrying out a single measurement of the response generated by the sensor upon exposure to a calibration fluid for which the magnitude of the characteristic in question is known; calibration in this manner is referred to hereafter as "single-point calibration". The preferred embodiment, described in detail later, of a single-use measuring device for use in a method according to the present invention, and which is intended inter alia for the measurement of the concentrations of sodium ion and potassium ion in a sample of whole blood, incorporates ion-selective potentiometric sodium and potassium sensors whose response is calibrated by single-point calibration, the conditioning fluid in this preferred embodiment being an aqueous solution comprising sodium and potassium ions in known concentrations.

However, if desired, two-point or multiple point calibration of sensor response may be carried out; for example, by a procedure involving the successive exposure of the sensing surface part of the sensor to an appropriate number of conditioning (calibration) fluids contained in separate chambers positioned sequentially in the measuring device, the chambers being separated from each other by rupturable wall parts comprising areas which are mutually and with respect to the direction of movement of the sensor positioned in a linear fashion, and through which the sensor can pass successively.

A preferred embodiment, described in detail later, of an ion-selective potentiometric electrode, for use, for example, in a method according to the present invention, is based on an electrically conducting carbon-containing layer which is coated with an ion-selective membrane comprising an ion-selective material. Ion-selective electrodes of this type are well suited to single-point calibration, in that they can be manufactured highly reproducibly and data for their calibration can be determined batchwise at the time of manufacture.

The term "conditioning fluid" as used here denotes a fluid which functions as one or both of the following:

a calibration fluid for the calibration of the response of the sensor in relation to the magnitude of the characteristic, the calibration fluid containing a known concentration of chemical species, a fluid for the preparation of the sensor prior to the use of the sensor in measuring the characteristic such that measurement of the characteristic can take place without further treatment of the sensor, and which, in addition, may function as one or more of the following:

a reference fluid for a reference electrode;

a fluid for establishing a fluid junction between a reference fluid and a sample fluid;

a fluid for establishing a fluid junction between a reference fluid and a conditioning fluid;

The term "first wall part" as used here denotes a wall of the conditioning fluid chamber which constitutes a physical boundary between the inside and the outside of the chamber, but which is constructed either such that an aperture matching in size and profile the cross-section of the sensor is provided for the sensor, the perimeter of the aperture being equipped with sealing means which provide the above-mentioned fluid-tight seal around the sensor, the sensor in this case at all times traversing the wall, or such that it initially has no aperture for the sensor, thereby initially constituting an intact boundary between the inside and the outside of the chamber, but is ruptured by the sensor following movement of the sensor and the first wall part relative to each other, an aperture being formed which matches in size and profile the cross-section of the sensor, the perimeter of the aperture providing the above-mentioned fluid-tight seal around the sensor.

Depending upon the cross-sectional profile of the sensor, the above. mentioned sealing means can comprise, for example, a sealing ring, such as an "O"-ring made of natural or synthetic rubber or of some other elastomer material, which provides a substantially tight seal around the sensor.

Alternatively, for example, the first wall part itself may conveniently be made of a suitable material, e.g. a polymeric material with elastomeric properties or, in the case of aqueous fluids, hydrophobic properties (the efficacy, with respect to aqueous fluids, of the seal around the sensor which is provided by a non-elastomeric material is significantly enhanced when the material possesses hydrophobic properties), or both of these properties. which, either in those cases where the sensor at all times traverses the first wall part, or in those cases where the first wall part is ruptured by the sensor, provides a substantially tight seal around the sensor.

In a further aspect of the invention, a first wall part which is ruptured by the sensor comprises a weakened area, the rupturing of the first wall part by the sensor occurring within said area. This weakening can, for example, be brought about simply by fashioning the first wall part such that the thickness of the material of which it is made within the area in question is less than the thickness of the material in the surrounding regions of the first wall part. Irrespective of whether the first wall part is at all times traversed by the sensor, or is ruptured by the sensor, the seal established around the sensor must at least permit relative movement of the sensor and the first wall part without excessive frictional resistance to the movement, and substantially prevent contamination of the sample fluid by the conditioning fluid or vice versa.

It will be apparent that a satisfactory seal around the sensor is most readily achieved when that section of the body of the sensor which undergoes relative movement through the first wall part is substantially smooth and of substantially regular and uniform cross-sectional profile. It is thus advantageous that the contour of the sensing surface part of the sensor does not differ significantly from that of the surrounding regions of the body of the sensor. For example, in the case of a cylindrically formed sensor the curvature of the sensing surface part of the sensor about the cylinder axis should preferably be the same as that of the surrounding regions of the sensor body; furthermore, in a direction parallel to the cylinder axis the sensing surface should preferably be flush with the surface of the surrounding regions of the sensor body.

In the two closely related methods described earlier, above, the stage at which, and method by which the conditioning fluid is introduced into the conditioning fluid chamber is not specifically assumed. However, from the point of view of the functioning, reliability and shelf-life of several types of sensor, for example enzyme-based sensors for measurements on body fluids, where the activity of the enzyme is best maintained by keeping the enzyme-containing part of the sensor in a dry condition prior to use of the sensor, as well as from the point of view of fluid-tight storage and constancy of composition of the conditioning fluid prior to use of the measuring device in measurement of a characteristic, it is advantageous that the types of sensor in question are initially, i.e. while the measuring device is stored prior to use, out of contact with the conditioning fluid. This can, for example, be achieved by storing the conditioning fluid within the measuring device in such a way that it can be released into the conditioning fluid chamber when the characteristic is to be measured.

The present invention therefore also provides methods for measuring a characteristic which is a function of the concentration of one or more chemical species in a sample fluid, the measuring devices used being similar to those used in the methods described above but further comprising a store of conditioning fluid, said store either being adapted for a single release of conditioning fluid into the conditioning fluid chamber, or being adapted for repeated release of conditioning fluid into the conditioning fluid chamber.

In a further aspect of the invention, the conditioning fluid stored in a measuring device for use in accordance with the present invention is stored in a closed and rupturable pack, the packaging material of the pack being substantially fluid-tight, the release of the conditioning fluid from the pack preferably comprising the application of pressure to, optionally in combination with perforation of, the pack. In those cases where the conditioning fluid is a liquid, e.g. an aqueous solution as in the preferred embodiment and other embodiments of the invention as disclosed herein, it is desirable that the packaging material of the pack is not only substantially liquid-tight but is also substantially tight with respect to the vapour of the liquid in question, thereby ensuring that substantially no evaporation loss of liquid from the conditioning liquid takes place by diffusion of the vapour through the packaging material. As a non-limiting example of a suitable type of packaging material for an aqueous conditioning liquid may be mentioned a metallized plastic foil material, such as polyethylene foil coated with aluminium (the plastic foil being on the inside of the pack), which is chosen on the basis of its flexibility, mechanical strength, and substantial tightness and inertness towards the conditioning liquid and its vapour.

In clinical chemical applications of the present invention in which the sample fluids of interest are body fluids, it is in general desirable, not least for reasons of hygiene but also to avoid expending time and labour in cleaning sensors in between measurements, that the measuring device is used only once and then discarded. However, notably in the case of non-medical analytical applications, for example in field analyses in which measurements are made directly on large reserves of fluid, for example natural bodies of water, and under which circumstances intermediate cleansing of sensors is effectively unnecessary, it will often be an advantage to be able to re-use the measuring device with its content of conditioning fluid.

The present invention therefore also provides methods for measuring a characteristic which is a function of the concentration of one or more chemical species in a sample fluid, the methods differing from those described above in that either, in those cases where the conditioning fluid chamber of the measuring device is intended to be filled only once with conditioning fluid (either from a store of conditioning fluid within the measuring device, or by any other means, the measuring device is not discarded after one, but instead is discarded after more than one measurement of the characteristic, the discardment taking place before the conditioning fluid is no longer capable of properly exerting its conditioning function, or, in those cases where the measuring device comprises a store of conditioning fluid intended for repeated release of conditioning fluid into the conditioning fluid chamber, the measuring device is not discarded after one measurement of the characteristic, but is re-used such that the conditioning fluid in the chamber is replaced with a fresh portion of conditioning fluid from said store after each measurement of the characteristic, the measuring device being discarded before or when the store of conditioning fluid has been consumed.

A measuring device for use according to the invention may further comprise a sample fluid chamber adapted to contain the sample fluid containing the chemical species, the sample fluid chamber having inlet means for introducing the sample fluid into the sample fluid chamber and being partly defined by the first wall part, the sensor and the sample fluid chamber being movable relative to each other so as to transfer the sensing surface part of the sensor through the first wall part from a position where the sensing surface part of the sensor is inside the conditioning fluid chamber to a position where it is inside the sample fluid chamber, or vice versa.

Notably in clinical chemical analysis of body fluids, particularly of blood, it is highly desirable, not least from the point of view of protection of laboratory staff from contact with infectious agents that may be present in a body fluid, that after sample taking, no transfer of a body fluid sample from one container to another has to be carried out at any stage of the analysis procedure.

Thus, in a method according to the present invention wherein a measuring device comprising a sample fluid chamber is discarded after one measurement of the characteristic, the discardment may take place without any prior discharge of sample fluid or conditioning fluid from the measuring device.

When a measuring device in accordance with the invention comprises a sample fluid chamber, the sample fluid chamber may be further partly defined by a second wall part adapted to allow the sensor to pass through it and establish a seal around the sensor, the sensor traversing the second wall part before said use of the measuring device. The second wall part of such a measuring device is constructed such that an aperture matching in size and profile the cross-section of the sensor is provided for the sensor, and the seal around the sensor may be achieved in the same manner as described earlier, above, for a first wall part which is traversed at all times by the sensor. At no time during a measurement cycle does the sensing surface part of the sensor of a measuring device comprising a second wall part as defined here pass through the second wall part.

In a measuring device for use in accordance with the present invention which comprises a sample fluid chamber, movement of the sensor and the sample fluid chamber relative to each other so as to transfer the sensing surface part of the sensor through the first wall part from a position where the sensing surface part of the sensor is inside the conditioning fluid chamber to a position where it is inside the sample fluid chamber, or vice versa, will, unless the sensor at all times traverses both the first wall part and the second wall part and is of uniform cross sectional profile along that part of its length which moves within the sample fluid chamber, entail a pressure increase or decrease, respectively, in the sample fluid chamber; this pressure change will, especially in the case of fluids which are liquids, require pressure equalization in the sample fluid chamber.

In clinical chemical applications of the present invention, the requirement of eliminating any risk of operator contact with the contents of the sample fluid chamber (i.e. a body fluid) makes undesirable the use of a measuring device in which a part of the sensor body which has been in contact with the sample fluid can protrude from the measuring device, and in which there will, irrespective of the effectiveness of the seal of the second wall part around the sensor, inevitably be the possibility, however slight, of some leakage of body fluid from the sample fluid chamber via the latter seal.

However, from the point of view of simplicity of construction, a measuring device for use according to the present invention in which the sensor traverses both the first and second wall parts as described above, the movement of the sensor and the sample fluid chamber relative to each other thereby entailing substantially no pressure change in the sample fluid chamber, does have some advantages, and such a measuring device is quite practicable for non-medical analytical applications. Thus, embodiments of the present invention involve the use of a measuring device incorporating a second wall part traversed by the sensor, but in which the sensor of the measuring device further traverses the first wall part before said use of the measuring device, the sensor thereby traversing both the first and second wall parts at all times.

For some purposes it may be desirable that the sensing surface part of the sensor, or even the entire sensor body, of a measuring device as defined within the context of the present invention is initially, i.e. prior to measurement of a characteristic, positioned neither inside the conditioning fluid chamber nor, in cases where the measuring device comprises a sample fluid chamber, inside the sample fluid chamber. For example, it may in some cases be an advantage that the conditioning fluid be introduced directly into the conditioning fluid chamber at the time of manufacture of the measuring device, and that the sensor and the conditioning fluid chamber then be moved relative to each other, upon commencement of a measurement cycle, so as to position the sensing surface part inside the conditioning fluid chamber and thus expose the sensing surface part to the conditioning fluid.

Thus, in yet another embodiment of the present invention, a measuring device for use in any of the methods described above further comprises a third wall part which partly defines the conditioning fluid chamber, the third wall part being adapted to allow the sensor to pass through it and establish a seal around the sensor when the sensor traverses the third wall part, the sensor and the conditioning fluid chamber being movable relative to each other so as to transfer the sensing surface part of the sensor through the third wall part from a position where the sensing surface part of the sensor is outside the conditioning fluid chamber to a position where it is inside the conditioning fluid chamber. The third wall part may be of the same types as described earlier, above, for a first wall part, i.e. it may be such that the sensor traverses the third wall part before use of the measuring device, an aperture matching in size and profile the cross-section of the sensor being provided for the the sensor, the perimeter of the aperture being equipped with sealing means which provide a fluid-tight seal around the sensor, or it may be such that it initially has no aperture for the sensor, but is ruptured by the sensor following movement of the sensor and the third wall part relative to each other, an aperture being formed which matches in size and profile the cross-section of the sensor, the perimeter of the aperture providing a fluid-tight seal around the sensor. In cases where the third wall part is ruptured by the sensor, the third wall part may further comprise a weakened area, the rupturing of the third wall part by the sensor occurring within said area.

The broad principles underlying the construction of, and the sequence of sensor movement in various types of measuring device in accordance with the present invention are summarized in the drawings shown in FIGS. 1–6. In these drawings, and in other drawings described later, like numerals designate like parts.

BRIEF DESCRIPTION OF THE DRAWINGS

FIG. 1 is a cross-sectional view of an embodiment of a measuring device in accordance with the invention having a conditioning fluid chamber, a sample fluid chamber and a sensor which is axially displaceable between said chambers;

FIG. 2 shows a second embodiment of a measuring device having a conditioning fluid chamber, a sample fluid chamber and a sensor which is axially displaceable between said chambers;

FIG. 3 shows a third embodiment of a measuring device having a conditioning fluid chamber, a sample fluid chamber and a sensor which is axially displaceable between said chambers;

FIG. 4 shows a forth embodiment of a measuring device having a conditioning fluid chamber, a sample fluid chamber and a sensor which is axially displaceable between said chambers;

FIG. 5 shows a fifth embodiment of a measuring device in accordance with the invention having a conditioning fluid chamber and an external sample fluid holder;

FIG. 6 is an alternative embodiment of the measuring device illustrated in FIG. 5 which likewise has a conditioning fluid chamber and an external sample fluid holder;

FIG. 7 is an oblique view of another embodiment of a measuring device in accordance with the invention;

FIG. 8 is an oblique view of the measuring device of FIG. 7 shown in partial cutaway section;

FIG. 9 is a side cross-sectional view of the measuring device shown in FIGS. 7 and 8;

FIG. 10 is an oblique view of a measuring device in accordance with the present invention shown in combination with an analyzer for use therewith;

FIG. 11 is an oblique view of an ion selective potentiometric electrode of a measuring device in accordance with the invention;

FIG. 12 is a side cross-sectional view of another embodiment of an ion selective potentiometric sensor of a measuring device in accordance with the invention;

FIG. 13 is an enlarged side cross-sectional view of the ion selective potentiometric sensor shown in FIG. 12;

FIG. 14 is an oblique view of another embodiment of a measuring device shown in combination with an analyzer in accordance with the invention; and FIG. 15 is an oblique view of yet another alternative embodiment of a measuring device shown in combination with an analyzer in accordance with the invention.

FIG. 1 illustrates a measuring device (1) incorporating a sample fluid chamber (2), equipped with a sample fluid inlet/outlet (3). A sensor (5), comprising a sensor body (7), a sensing surface part (9) and, optionally, a contact point (11), traverses a first wall part (13) which separates a conditioning fluid chamber (15) and the sample fluid chamber (2). A second wall part (17) partly delimits the sample fluid chamber (2), and a third wall part (19) partly delimits the conditioning fluid chamber (15). The sensing surface part (9) of the sensor (5) is initially exposed to a conditioning fluid (21) in the conditioning fluid chamber (15). The sensor (5) is then moved as indicated by the arrow in the figure so as to expose the sensing surface part (9) to a sample fluid (23) in the sample fluid chamber (2).

FIG. 2 illustrates a measuring device (1) which closely resembles that shown in FIG. 1, except that a sensing surface part (9) of a sensor (5) is first exposed to a sample fluid (23) in a sample fluid chamber (2). The sensor (5) is then moved as shown by the arrow in the figure so as to expose the sensing surface part (9) to a conditioning fluid (21) in a conditioning fluid chamber (15).

FIG. 3 illustrates a measuring device (1) in which a sensing surface part (9) of a sensor (5) is initially inside a conditioning fluid chamber (15) but is not exposed to a conditioning fluid (21). The conditioning fluid (21) is initially stored in a rupturable pack (25). The conditioning fluid (21) is released from the rupturable pack (25) into the conditioning fluid chamber (15) by application of pressure from an external pressure plunger (27), the pressure plunger (27) not being a part of the measuring device (1) itself. After exposure of the sensing surface part (9) of the sensor (5) to the conditioning fluid (21), the sensor (5) is then moved as shown by the arrow in the figure so as to expose the sensing surface part (9) to a sample fluid (23) in a sample fluid chamber (2).

FIG. 4 illustrates a measuring device (1) in which a sensor body (7) of a sensor (5) initially traverses only a third wall part (19), a sensor surface part (9) of the sensor (5) initially being exposed to a conditioning fluid (21) in a conditioning fluid chamber (15). The sensor (5) is then moved as shown by the arrow in the figure, whereby a first wall part (13) is ruptured by the sensor (5) and the sensing surface part (9) becomes exposed to a sample fluid (23).

Whereas FIGS. 1.4 illustrate measuring devices to be used in accordance with the present invention which incorporate sample chambers, FIGS. 5 and 6 illustrate measuring devices to be used in accordance with the present invention which are intended for use in conjunction with an external sample fluid holder (29):

FIG. 5 illustrates a measuring device (1) in which a sensing surface part (9) of a sensor (5) is initially exposed to a conditioning fluid (21) in a conditioning fluid chamber (15). The sensor (5) is then moved as shown by the arrow in the figure so as to position the sensing surface part (9) outside the conditioning fluid chamber (15), and the sensing surface part (9) is then exposed to a sample fluid (23) contained in a sample fluid holder (29).

FIG. 6 illustrates a measuring device (1) in which a sensing surface part (9) of a sensor (5) is initially inside a conditioning fluid chamber (15) but is not exposed to a conditioning fluid (21). The conditioning fluid (21) is initially contained in a rupturable pack (25). The conditioning fluid (21) is released into the conditioning fluid chamber (15) by the application of pressure from an external pressure plunger (27) to the rupturable pack (25), the pressure plunger (27) not being a part of the measuring device (1) itself. After exposure of the sensing surface part (9) to the conditioning fluid (21), the sensor (5) is then moved as shown by the arrow in the figure so as to position the sensing surface part (9) outside the conditioning fluid chamber (15), and the sensing surface part (9) is then exposed to a sample fluid (23) contained in a sample fluid holder (29).

In measuring devices constructed according to the principles illustrated by the above FIGS. 1–6, as well as in measuring devices to be described below, one or more of the various wall parts (13, 17 and 19) may be fabricated from material which is the same as the basic constructional material of the measuring device as a whole (1).

As discussed earlier, above, in the case of measuring devices comprising an electrochemical sensor, measurement of the sensor response requires the provision of a suitable electrochemical reference sensor. In FIGS. 1–6, no explicit provision is made for the inclusion of an electrochemical reference sensor in any of the various measuring devices, but such a reference sensor could advantageously be placed in a conditioning fluid chamber (15) of any measuring device constructed according to the principles illustrated in these figures. Alternatively, a reference sensor could, for example, be incorporated in a separate part of a body (7) of a measuring sensor (5).

It will be apparent from the description herein of the present invention that the principles of the construction of a measuring device to be used in accordance with the invention are not limited to those shown in FIGS. 1–6. For example, in the same way that the measuring devices illustrated in FIGS. 1 and 2 differ in essence only in the sequence of exposure of the sensing surface part (9) of the sensor (5) to the conditioning fluid (21) and the sample fluid (23), respectively, a measuring device similar to that illustrated in FIG. 3 but differing from it in that the sensing surface part (9) of the sensor (5) is initially exposed to the sample fluid (23) in the sample fluid chamber (2), after which the sensor is moved so as to position the sensing surface part (9) inside the conditioning fluid chamber (15) and exposed to the conditioning fluid (21), can equally well be envisaged. Similarly, a measuring device related to that illustrated in FIG. 4 can be envisaged in which the sensor body (7) initially traverses the second wall part (17) instead of the third wall part (19), the sensing surface part (9) of the sensor (5) initially being exposed to the sample fluid (23); the sensor (5) is then moved so as to rupture the first wall part (13) and expose the sensing surface part (9) to the conditioning fluid (21) in the conditioning fluid chamber (15).

Other combinations of the principles illustrated in FIGS. 1–6 and described herein can also be envisaged and are intended to be encompassed within the scope of the present invention.

FIGS. 7, 8 and 9 illustrate a preferred embodiment of a measuring device (1), for example for use in accordance with the present invention, which is intended for the measurement of concentrations of sodium, potassium, glucose and haemoglobin in freshly drawn whole blood.

As indicated by comparing FIG. 7 with FIGS. 8 and 9, the latter two of which show the inner construction of the measuring device (1), it can be seen that the measuring device as supplied, packed in a foil bag (71), is equipped with a standard luer fitting (73) for affixing a standard hypodermic syringe needle (75), and a cylindrical outer protecting cover (77) which can be moved parallel with the long axis of the measuring device (1) so as to cover the syringe needle (75). The sequence of operations for taking a blood sample for determination of the above-mentioned concentrations of chemical species is as follows:

The foil bag (71) enclosing the measuring device (1) with its protective cover (77) is removed, and the luer fitting (73) is equipped with a sterile hypodermic syringe needle (75) [alternatively, the measuring device (1) may be attached, via the luer fitting (73), to a catheter (not shown)]; the needle is then inserted into a suitable vein or artery of the patient. If the patient's blood pressure is adequate, blood will flow, via a one-way valve (85), into a sample fluid chamber (2) and further into the measuring device until it reaches a hydrophobic filter (87) which allows the passage of air but prevents the passage of blood. If the patient's blood pressure is insufficient to enable blood to flow spontaneously into the measuring device, drawing of blood can be facilitated with the aid of a vacuum generating means (89) which generates a slight vacuum when a vacuum plunger (91) is depressed. Adequate filling with blood can be checked visually with the aid of a window (103) which is visible through a hole (72) in the outer protecting cover (77). Finally, the protecting cover (77) is slid forwards to cover the syringe needle (75); the measuring device (1) with the protecting cover (7) in the forward position can be seen in FIG. 10.

The entire measuring device (1), equipped with its sensors (5) comprising a sodium-selective potentiometric electrode (5a), a potassium-selective potentiometric electrode (5b) and an optical glucose sensor (5c), and with a silver/silver chloride reference electrode (93), all of which are positioned in guiding channels (94) thereto, is then transferred to an analyzer (110), shown in FIG. 10, for derivation of the concentrations of the above-mentioned chemical species. The analyzer (110), which is intended for connection to a suitable electric power source, and which together with the measuring device (1) constitutes an example of an analysis system according to the invention, comprises a sliding receptacle (114) to hold the measuring device (1). The analyzer (110) is switched on with the aid of an on/off switch (112), and the measuring device (1) with its protecting cover (77) in the forward position covering the syringe needle (75) is placed in the sliding receptacle (114). The sliding receptacle (114) is then pushed into position in the analyzer (110). Manufacturers data, in the form of a code (119), e.g. a bar-code or magnetic code, supplied with the measuring device (1) are then read by the analyzer (110). Patient data and data concerning the blood sample can be keyed into the analyzer using a keyboard (116). The measurement cycle is then initiated by depressing an activating switch (118).

The measurement cycle then takes place as follows: upon depressing the activating switch (118) electrical contact with sensor response output means in the form of contact points (11) of the three electrodes (5a, 5b, 93) is established, and an internal pressure plunger mechanism (not shown) in the analyzer (110) exerts pressure via the hole (72) in the protecting cover (77), on a flexible pressure membrane (26), thereby rupturing a rupturable pack (25) contained under the pressure membrane (26) and releasing a conditioning fluid (21) into a conditioning fluid chamber (15); during the release of the conditioning fluid (21) into the conditioning fluid chamber (15), air is released from the conditioning fluid chamber (15) via a vent (97) equipped with a hydrophobic filter (99) which allows the passage of air but prevents the passage of conditioning fluid. The sensing surface parts (9) of the sodium-selective electrode (5a) and the potassium-selective electrode (5b), and the sensing surface part (10) of the reference electrode (93), which initially are inside the conditioning fluid chamber (15) while the three electrodes (5a, 5b and 93) traverse a third wall part (19) which provides a seal around the three electrodes, are thus exposed to the conditioning fluid (21). After an interval specified in the data read by the analyzer (110) from the code (119), which interval allows the electrodes (5a, 5b and 93) to become equilibrated, the electric potential of the sodium- and potassium-selective electrodes (5a, 5b) relative to the reference electrode (93) is transmitted via sensor response transmission means, such as electrical conduits, to the sensor response registering means of the analyzer (110), such as microprocessor or microcomputer means, which then carries out an internal single-point calibration of the electric potential of the sodium- and potassium-selective electrodes (5a, 5b) on the basis of the concentrations of sodium ion and potassium ion in the conditioning fluid (21) and other calibration data read by the analyzer (110) from the code (119) before the start of the measurement cycle. An internal mechanism (not shown) in the analyzer (110) then pushes the electrodes (5a, 5b and 93), which are guided by guiding channels (96 and 98), so as to rupture weakened areas (92) of a first wall part (13); the electrodes (5a, 5b and 93) then become positioned such that the sensing surface parts (9) of the sodium- and potassium-selective electrodes (5a, 5b) are exposed to the blood in the sample fluid chamber (2), and a liquid junction groove (95) in the reference electrode (93) traverses the first wall part (13) so as to establish a liquid junction between the conditioning fluid (21) to which the sensing surface part (10) of the reference electrode (93) remains exposed and the blood sample in the sample fluid chamber (2). The electrode responses are transmitted to the analyzer and registered therein as described above in connection with the description of the exposure of the electrodes to the conditioning fluid. Pressure build-up in the conditioning fluid chamber (15) due to displacement of conditioning fluid (21) upon movement of the electrodes (5a, 5b and 93) is prevented by the escape of air from the vent (97), the volume of the conditioning fluid chamber (15) being sufficiently greater than the sum of the volume of the conditioning fluid (21) and the displacement volume of the electrodes (5a, 5b and 93) to allow adequate free air space. At the same time as the electrodes (5a, 5b and 93) are moved, an internal mechanism (not shown) in the analyzer (110) also moves the optical glucose sensor (5c) so as to rupture a weakened area (92) of the first wall part (13) and expose a tip (14) of the glucose sensor (5c) to the blood sample in the sample fluid chamber (2). The glucose sensor (5c), the tip of which (14) is equipped with a glass-fibre filter that prevents the passage of red blood cells, absorbs plasma from the blood sample by capillary action, whereupon a reaction producing a colour occurs between glucose in the blood plasma and reagents with which the glucose sensor (5c) is impregnated. The intensity of colour of a surface (12) of the glucose sensor, registered via a window (101), is then recorded reflectometrically by the analyzer (110) and converted to glucose concentration on the basis of data read by the analyzer (110) from the code (119) before the start of the measurement cycle. The capillary absorbtion of blood by the glucose sensor (5c) also serves to prevent pressure build-up in the sample fluid chamber (2) as a result of the entry of the various sensors (5a, 5b, 5c and 93) into the sample fluid chamber (2), the glucose sensor (5c) being dimensioned so as to at least be able to absorb the volume of blood displaced both by itself and by the three electrodes (5a, 5b and 93).

The analyzer (110) also performs a spectrophotometric measurement of the level of haemoglobin in the blood sample: a portion of the blood sample contained in a cuvette (102) of known thickness which constitutes an extension of the sample fluid chamber (2) is haemolysed essentially instantaneously by a haemolysing agent contained within the cuvette (102), the haemoglobin content of the red blood cells in the portion of blood sample within the cuvette thereby being released. The light absorption by the haemoglobin is then registered by the analyzer (110) via the window (103), and the haemoglobin concentration in the blood sample is then derived on the basis of this light absorption and the data read from the code (119) by the analyzer (110).

The analytical results concerning the concentrations of sodium, potassium, glucose and haemoglobin, derived from the registered sensor responses, as well as patient data etc. keyed into the analyzer by the operator, can be read from a display (120) and are also recorded on chart paper (122). Upon completion of the measurement cycle, the measuring device complete with contents, and with its protecting cover (77) remaining in the forward position so as to cover the syringe needle (75), is removed from the sliding receptacle (114) and disposed of, for example by incineration.

The principles illustrated in FIGS. 7, 8 and 9 can be further elaborated in that more than one conditioning fluid chamber and, optionally, more than one store of individual conditioning fluid (with appropriate pressure-applying means) can be provided in the device to allow for differences in conditioning requirements between different types of sensors. FIGS. 7, 8 and 9 can also serve to illustrate a preferred embodiment of a measuring device in which the only sensor incorporated is a sensor requiring no conditioning, namely an optical glucose sensor (5c). In such a measuring device, the following components shown in the figures are not required:
the flexible pressure membrane (26),
the rupturable pack (25) containing the conditioning fluid (21),
the conditioning fluid chamber (15),
the vent (97) together with the hydrophobic filter (99),
the third wall part (19),
the electrodes (5a, 5b and 93),
the three sets of guiding channels (94, 96 and 98) for the electrodes,
and the three weakened areas (92) for rupture of the first wall part (13) by the electrodes.

Filling of the sample fluid chamber (2) of such a measuring device with blood, and its placement in an analyzer (110), take place as described before, above. The measurement cycle differs, however, from that described above in that only movement of the glucose sensor (5c) is required, followed by a reflectometric colour intensity measurement by the analyzer (110) and, optionally, a spectrophotometric measurement of the level of haemoglobin in the blood sample. The analyzer in this case therefore does not require the following:
means for establishing electrical contact with electrodes.
an internal mechanism for moving electrodes,
an internal pressure plunger mechanism,
means for carrying out calibration calculations in connection with electrode calibration,
and means for converting electrode responses to concentrations of chemical species.

FIG. 11 illustrates a unit (6) comprising a sodium-selective potentiometric electrode (5a), a potassium-selective potentiometric electrode (5b) and a silver/silver chloride reference potentiometric electrode (93)m, all three electrodes (5a, 5b and 93) having button-shaped sensing surface parts (9). An insulating layer (127) insulates electrical connection paths (128) connecting electrical contact points (11) with the sensing surface parts (9 and 10) of the elctrodes (5a, 5b and 93).

The unit (6) is a non-limiting example of an alternative to the individual electrodes (5a, 5b and 93) shown in FIGS. 8 and 9. The unit (6) is moveable so as to subject the electrodes (5a, 5b and 93) to the same sequence of movements, and their sensing surface parts to the same sequence of exposure to conditioning and sample fluids, as the individual electrodes (5a, 5b and 93) shown in FIGS. 8 and 9.

FIGS. 12 and 13 illustrate schematically (i.e. the relative sizes of the individual parts as indicated in the figures are not necessarily correct) the construction of a preferred embodiment of a new type of ion-selective potentiometric sensor for use, for example, in an electrode unit similar to that (6) shown in FIG. 11. This new type of ion-selective potentiometric sensor incorporates a thin and substantially uniform electrically conducting layer (131) which comprises a carbon material, such as carbon, carbon black or graphite, the carbon material being in the form of particles of size at the most 100 $p$m, and a binder comprising a polymer, such as an acrylic or epoxy polymer, PVC, PUR or polystyrene. The layer (131). which may be of thickness 5–500 $\mu$m, is deposited on a substrate (133), an aperture (134) being provided in the substrate (133) through which a part (131$a$) of the carbon-containing material of the layer (131) protrudes. This protruding part (131$a$) is used to establish electrical contact to a contact point, e.g. a contact point of the type (11) shown in FIG. 11. The carbon-containing layer (131) is coated with an ion-selective membrane (135) comprising an ion-selective material, such as an ionophore or an ion exchanger, and a matrix comprising a polymer, such as a polymer of one of the types mentioned above in connection with the carbon-containing layer (131). The method by which the ion-selective membrane (135) is coated onto the carbon-containing layer (131) is chosen such as to ensure good contact between the ion-selective membrane (135) and the carbon-containing layer (131) by the creation of a mixed-interphase zone (137) between the ion-selective membrane (135) and the carbon-containing layer (131); this can, for example, suitably be achieved by the use of a solvent which at least partly dissolves the binder of the carbon-containing layer (131) and the matrix material of the ion-selective membrane (135).

French patent application FR 87-17 437 discloses advantages associated with the provision of a mixed-interphase zone.

Ion-selective potentiometric sensors of the type illustrated in FIGS. 12 and 13 are characterized by a short dry-to-wet equilibration time, rendering them well suited to applications, such as those described herein, in which dry storage of sensors prior to use is an advantage.

FIGS. 14 and 15 illustrate two further preferred embodiments of a measuring device and an analyzer for use according to the present invention, both of which are intended for non-medical analyses of fluids which are liquids:

In FIG. 14, a measuring device (1), equipped with a data code (119), for example in the form of a bar-code or magnetic code, is positioned in an analyzer (150) as indicated by the dashed lines in the figure, the analyzer (150) having been switched on with the aid of an on/off switch (112); electrical contact to a contact point (11) of a sensor (5) is thereby established. The manufacturers data contained in the code (119) on the measuring device (1) are then read by the analyzer (150). The measurement cycle is initiated by depressing a contact (125), whereupon a pressure plunger (not shown) within the analyzer (150) moves downwards, through an opening (28) in the measuring device (1), and ruptures a rupturable pack (25), releasing a conditioning fluid (21) into a conditioning fluid chamber (15). A sensing surface part (9) of the sensor (5) thus becomes exposed to the conditioning fluid (21). After an interval during which the sensor (5) is conditioned [and, in the case of sensors requiring calibration, any necessary sensor response calibration measurements are carried out by the analyzer], the duration of the interval being predetermined according to the data read by the analyzer (150) from the code (119) on the measuring device (1), an internal mechanism (not shown) of the analyzer (150) moves the sensor (5) downwards so as to position the sensing surface part (9) of the sensor (5) outside the conditioning fluid chamber (15). A lifting stage (129) then raises a sample fluid holder (29) containing a sample fluid (23), so as to immerse the sensing surface part (9) of the sensor (5) in the sample fluid (23). The desired characteristic is then derived on the basis of the sensor response registered by the analyzer when the sensing surface part (9) of the sensor (5) is immersed in the sample fluid [and, in the case of sensors requiring calibration, on the sensor response registered by the analyzer (150) when the sensing surface part (9) of the sensor (5) is exposed to the conditioning fluid; in the case of electrochemical sensors this will require the provision of a reference electrochemical sensor (not shown)] and the data read by the analyzer (150) from the code (119) on the measuring device.

FIG. 15 shows a measuring device (1), equipped with a data code (119) as described above in connection with FIG. 14, and an analyzer (160) powered by a suitable self-contained electric power source (not shown) which together constitute a hand-held apparatus for carrying out field analyses. A sample fluid chamber (2) of the measuring device (1), filled with a sample fluid (23) via an inlet/outlet (3), is inserted into the bottom of the analyzer (160) as indicated by the dashed lines in the figure, whereupon electrical contact between the analyzer (160) and contact points (11) of sensors (5) is established, and a rupturable pack (25) containing a conditioning fluid (21) is ruptured by a pressure plunger (27) located in the analyzer (160), releasing the conditioning fluid (21) into a conditioning fluid chamber (15). Sensing surface parts (9) of the sensors (5) thus become exposed to the conditioning fluid (21). After an interval during which the sensors are conditioned [and, in the case of sensors requiring calibration any necessary sensor response calibration measurements are carried out by the analyzer], the duration of the interval being predetermined according to the data read by the analyzer (160) from the code (119) on the measuring device (1), the sensors (5) are moved downwards by a displacement arrangement (not shown in detail) which is operated manually by downward movement of a slider (140), thereby rupturing a first wall part (13) of the measuring device (1) and exposing the sensing surface parts (9) of the sensors (5) to the sample fluid (23) in the sample fluid chamber (2). The desired characteristics are then derived on the basis of the sensor responses registered by the analyzer (160) when the sensing surface parts (9) of the sensors (5) are exposed to the sample fluid [and, in the case of a sensor or sensors requiring calibration, on the sensor response(s) registered by the analyzer (160) when the sensing surface part(s) (9) of the sensor(s) (5) is/are exposed to the conditioning fluid (21); in the case of electrochemical sensors this will require the provision of a reference electrochemical sensor (not shown)] and the data read by the analyzer (160) from the code (119) on the measuring device (1).

I claim:

1. A measuring device for measuring the concentration of glucose in a sample of whole blood, comprising:
   a housing;
   a glucose sensor;
   a sample fluid chamber adapted to contain the whole blood sample, the housing having sample inlet means for introducing the sample into the sample fluid chamber;
   the glucose sensor having a front face constituting at the time of measuring a wall part of the sample fluid chamber and comprising indicator means and a filter layer interposed between the indicator means and the sample fluid chamber;
   said filter layer being capable to induce by capillary action part of the sample to flow through the filter to substantially separate plasma containing the glucose from red blood cells contained in the whole blood and said indicator means being capable to react with glucose for indicating the concentration of glucose in the blood.

2. The measuring device of claim 1, wherein the indicator means comprises an indicator/enzyme composition.

3. The measuring device of claim 1, wherein the sample inlet means comprises a fitting adapted from attachment of a syringe needle or a catheter.

4. The measuring device of claim 1, wherein one or more additional sensors selected form body fluid component sensors including potassium sensors and sodium sensors re arranged within the housing of the measuring device.

* * * * *

UNITED STATES PATENT AND TRADEMARK OFFICE
CERTIFICATE OF CORRECTION

PATENT NO. : 5,208,147

DATED : May 4, 1993

INVENTOR(S): HENRIK KAGENOW ET AL.

It is certified that error appears in the above-identified patent and that said Letters Patent is hereby corrected as shown below:

Column 20, line 49: After "selected" delete "form" and insert --from--.

Column 20, line 51: After "sensor" delete "re" and insert --are--.

Signed and Sealed this

Eighteenth Day of January, 1994

Attest:

BRUCE LEHMAN

Attesting Officer   Commissioner of Patents and Trademarks